United States Patent
Shi et al.

(10) Patent No.: US 9,284,648 B2
(45) Date of Patent: Mar. 15, 2016

(54) PROCESS AND MATERIAL SOLUTION TO REDUCE METAL ION RELEASE FOR IMPLANTABLE MEDICAL DEVICE APPLICATION

(75) Inventors: Alan Shi, Plymouth, MN (US); Bernard Li, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 441 days.

(21) Appl. No.: 13/447,873

(22) Filed: Apr. 16, 2012

(65) Prior Publication Data

US 2012/0273090 A1    Nov. 1, 2012

Related U.S. Application Data

(60) Provisional application No. 61/479,583, filed on Apr. 27, 2011.

(51) Int. Cl.
*A61L 27/50* (2006.01)
*C23F 1/00* (2006.01)
*A61L 27/04* (2006.01)

(52) U.S. Cl.
CPC ............. *C23F 1/00* (2013.01); *A61L 27/045* (2013.01); *A61L 27/50* (2013.01); *A61L 2400/18* (2013.01)

(58) Field of Classification Search
CPC ........... C23F 1/00; C23C 22/02; B32B 15/01; A61L 27/50; A61L 27/45; A61L 2400/18; C22C 18/03; C22C 18/05; C22C 18/051; C22C 18/056; C22C 18/057; C22C 18/07; C22C 27/06
See application file for complete search history.

(56) References Cited

U.S. PATENT DOCUMENTS

2005/0234545 A1    10/2005    Su et al.

FOREIGN PATENT DOCUMENTS

EP    2233159    9/2010

*Primary Examiner* — Lois Zheng

(57) ABSTRACT

The invention describes a method and compositions where the presence of cobalt and or nickel have been depleted from the surface layer(s) of a cobalt, chromium, nickel containing alloy.

22 Claims, 5 Drawing Sheets

PROCESS AND MATERIAL SOLUTION TO REDUCE METAL ION RELEASE FOR IMPLANTABLE MEDICAL DEVICE APPLICATION

CROSS REFERENCE TO RELATED APPLICATIONS

This application claims benefit under 35 U.S.C. §119(e) to U.S. Provisional Patent Application Ser. No. 61/479,583, filed Apr. 27, 2011, the contents of which is incorporated herein by reference in its entirety.

FIELD OF THE INVENTION

The invention relates generally to processes to modify a metal surface having cobalt and nickel in the composition as well as uses thereof.

BACKGROUND OF THE INVENTION

Implantable medical devices (IMDs) are used to produce therapeutic results in a patient and for monitoring physiologic parameters of a patient. Examples of IMDs include implantable drug infusion pumps, implantable neurostimulators, implantable cardioverter defibrillators, implantable cardiac pacemakers, and cochlear implants. Most of these IMDs often provide an electrical output or contain electrical circuitry to perform their intended functions. These devices are typically powered by a battery contained within the housing of the implantable medical device.

Cobalt/Nickel alloys are known and are often used in IMDs. For example, MP35N (35% Ni, 20% Cr, 10% Mo and approximately 35% Co by weight) is a cobalt based multi-phase alloy with excellent mechanical properties and corrosion resistance. MP35N has been used, for example, in conductor coils, spinal products, stents and various parts in implantable infusion pumps.

Release of Ni from an alloy, such as MP35N, is a concern because a small percentage of the general population shows Ni sensitivity. Co ion release is also a concern for electrical leads because, for example, polyurethane insulation about the lead may be subjected to metal ion oxidation (MIO). This oxidation can cause the polyurethane to degrade and allow for shorting of the electrode under physiological conditions.

Therefore, a need exists for a process and materials that overcomes one or more of the current disadvantages noted above.

BRIEF SUMMARY OF THE INVENTION

The present invention surprisingly provides chromium, cobalt, nickel alloys that are surface treated such that cobalt or nickel does not leach from the alloy in an appreciable amount under physiological conditions. A process is provided to surface treat cobalt, nickel and chromium alloys, such as MP35N, where the treated alloy surface releases less than 1 ng/mm$^2$, in particular less than 0.75 ng/mm$^2$ and most particularly 0.5 ng/mm$^2$ cobalt or nickel over a 16 week period under static soaking conditions at 37° C.

The surface of the alloy is treated with nitric acid at elevated temperatures for a given period of time. Generally, the nitric acid is from about 15% to about 30% by volume, with the remainder being water. The process is generally conducted at an elevated temperature range of from about 20° C. to about 100° C. over a period of about 30 minutes to about 3 hours, in particular from about 30 minutes to about 2.5 hour and most particularly from about 90 minutes to about 2 hours. The nitric acid treatment can be repeated two or more times.

The resultant surface treated cobalt, nickel and chromium alloy has reduced cobalt and/or nickel content at the surface. As such, release of Ni into a physiological environment is greatly reduced or eliminated; at least a 10 fold reduction, more particularly a 20 fold reduction, of Ni from the surface versus Ni content in the bulk of the alloy is achieved. Similarly, a 10 fold reduction, more particularly a 20 fold reduction, of Co from the surface of the alloy is achieved versus the Co content contained in the bulk alloy.

Another advantage of the surface treated cobalt, nickel and chromium alloy is that leaching of Co ion from the surface is greatly reduced or eliminated, such that oxidation of polymers, e.g., polyurethanes about electrical leads is reduced or eliminated. Thus MIO of the polymer is reduced or eliminated.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed descriptions are to be regarded as illustrative in nature and not restrictive.

DETAILED DESCRIPTION

Figure 1:
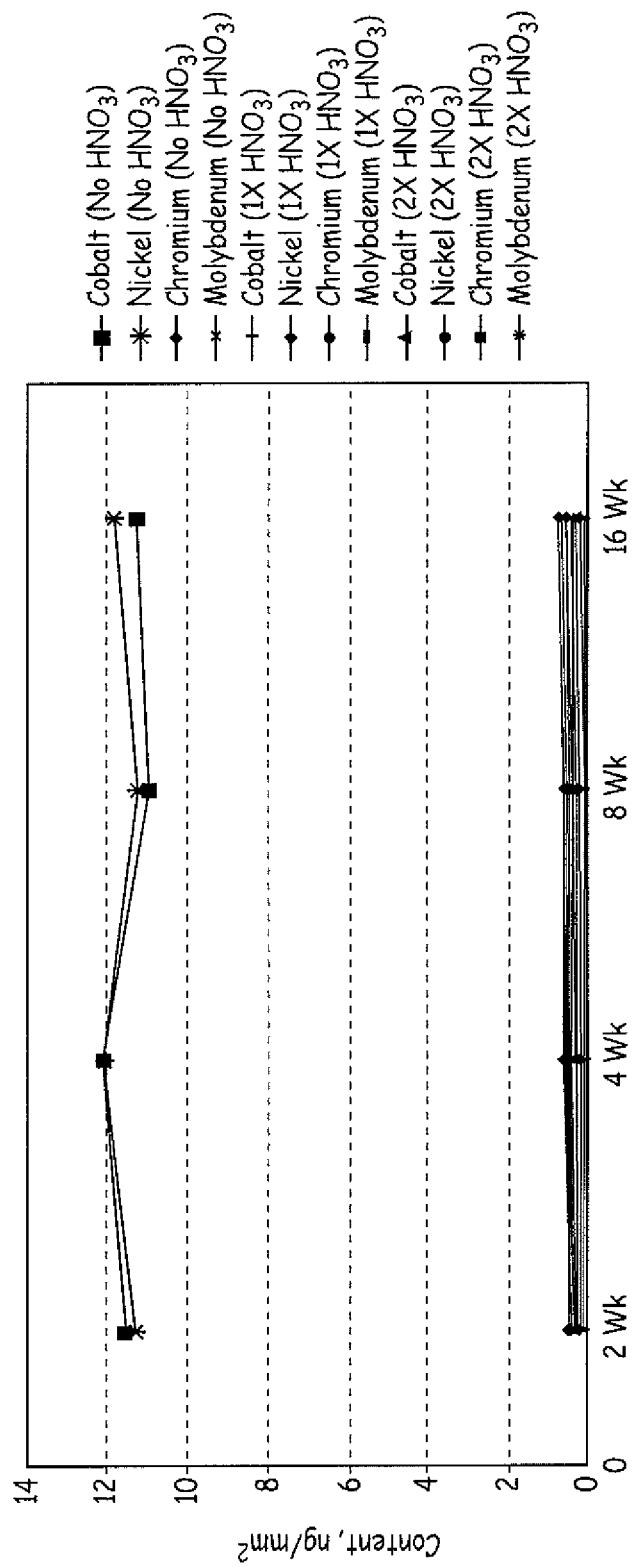
FIG. 1 provides metal ion release data showing comparison of no nitric acid treatment vs. once and twice nitric acid treatment.

In the specification and in the claims, the terms "including" and "comprising" are open-ended terms and should be interpreted to mean "including, but not limited to . . . ." These terms encompass the more restrictive terms consisting essentially of and "consisting of."

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", "characterized by" and "having" can be used interchangeably.

Unless defined otherwise, all technical and scientific terms used herein have the same meanings as commonly understood by one of ordinary skill in the art to which this invention belongs. All publications and patents specifically mentioned herein are incorporated by reference in their entirety for all purposes including describing and disclosing the chemicals, instruments, statistical analyses and methodologies which are reported in the publications which might be used in connection with the invention. All references cited in this specification are to be taken as indicative of the level of skill in the art.

Nothing herein is to be construed as an admission that the invention is not entitled to antedate such disclosure by virtue of prior invention.

In one embodiment, a surface modified alloy is provided that has reduced Co and/or Ni metal ion release from the alloy. Such treated alloys can be used for various implantable medical devices (IMDs) including, but not limited to, implantable drug infusion pumps, implantable neurostimulators, implantable cardioverter defibrillators, implantable cardiac pacemakers, electrical leads, conductor coils, connector blocks, implantable stents, bellows and cochlear implants.

In one aspect, the alloy is a cobalt based multi-phase alloy with excellent mechanical properties and corrosion resistance. A suitable alloy is MP35N which comprises about 35% nickel (Ni), about 20% chromium (Cr), about 10% molybdenum (Mo) and about 35% cobalt (Co) by weight. MP35N comes in various grades so that additional metals may be present, such as titanium (Ti). Generally, the titanium content of the alloy is less than or equal to 0.01% by weight.

Other suitable chromium, nickel and cobalt alloys include, for example Elgiloy, and cobalt/chromium based alloys such as ASTM F75, F90, F563, F799 and F1058. Other metals present in the alloys can include, for example, molybdenum, iron and/or tungsten.

Interestingly, titanium containing alloys tend to be thicker to retain mechanical strength, hence they are less desirable than those alloys with little or no titanium. For example, titanium alloys aren't especially useful as springs in a medical device as the required thickness of the spring would increase the size of the device which is undesirable. Consequently, the present invention provides Co/Ni/Cr treated alloys that are stronger and thinner than titanium alloys, providing an advantage for the preparation of mechanical devices, such as springs, where decreased thickness while retaining strength are important characteristics.

In one aspect, the alloy is treated with nitric acid at an elevated temperature for a period of time. Nitric acid has been found to be very effective as it passivates the alloy surface and removes Ni and/or Co ion from the surface and to a depth of at least 5 nm, in particular 10 nm and more particularly about 20 nm. Other acids, such as hydrofluoric acid are not desirable as it is believed that fluoride ion would attack the alloy surface and make it brittle. If titanium is present, the HF would attack the titanium causing dissolution of the alloy. Hydrochloric acid and sulfuric acid are also not desirable as these acids corrode chromium, nickel, cobalt alloys, such as MP35N.

In one embodiment, addition of nitrates or nitrite to the nitric acid solution, such as sodium nitrate or potassium nitrate, can be problematic and are not included as additives. In another embodiment, use of buffering solutions prior to nitric acid treatment, such as aqueous sodium bicarbonate, sodium carbonate and/or sodium hydroxide are not generally used prior at nitric acid treatment. Lastly, phosphoric acid has been found to be too weak to passivate the alloy surface. These treatments have been used to clean metal surfaces but generally do not achieve the aim of the present invention, the consistent removal of Co and/or Ni from the metal surface.

The surface of the alloy is treated with an aqueous solution of nitric acid. The alloy part is placed in a manner that the aqueous nitric acid solution covers the entire surface of the part. Generally the nitric acid content is from about 15% to about 55% by volume. Treatment times can be varied from about 30 minutes to about 3 hours, more particularly from about 20 minutes to about 2 hours and most particularly from about 90 minutes to about 2 hours. The surface modification treatment is generally conducted at a temperature of from about 20° C. to about 100° C., more particularly about 60° C.

After treatment with nitric acid, the alloy part is rinsed with deionized water within 10 minutes after removal from the nitric acid solution. In particular the alloy part is rinsed for a period of at least 20 minutes with flowing deionized water and then dried. This process can be repeated two or more times to achieve the desired surface effect.

In one aspect, the surface of the alloy is first cleaned with an alkaline aqueous solution containing ionic and non-ionic ingredients and chelating agents, such as MICRO-90® for between about 30 minutes and 2 hours at a temperature from about 100° F. to about 160° F. with sonication. Typically the cleaning solution has a concentration of surfactant/agents of about 0.01% to about 10% by weight, more particularly from about 1% to about 5% and most particularly about 1.5 to about 3% by weight. The alloy is then rinsed and sonicated in deionized water.

The nitric acid treated alloy composition provides that alloy releases less than 1 $ng/mm^2$, in particular less than 0.75 $ng/mm^2$ and most particularly less than 0.5 $ng/mm^2$ cobalt or nickel over a 16 week period under static soaking conditions at 37° C.

The treated alloy provides at least three advantages over current chromium, nickel, cobalt alloys. First, the amount of nickel that is released from the treated alloy is at an acceptable level for patients with Ni sensitivity. Second, it is desirable to reduce Ni release from an alloy that is in direct contact with cerebrospinal fluid such as where direct drug delivery is required. Third, Co ions can cause MIO on polyurethane insulator leads and results in failure of the leads. The process and surface treated alloys described herein avoid the release of Co ions and minimize or eliminate MIO of such leads. Currently, leads are often wrapped with a coating such as ETFE or PTFE to prevent oxidation by MIO. Hence, the current process/treated alloy eliminates the need and cost of an extra coating on a lead. Still another advantage is that the bulk properties of the alloy remain unchanged; only approximately 20 nm or less of the depleted surface of the alloy has been altered to remove the unwanted Co or Ni ions leaving a Cr and Mo surface.

The following paragraphs enumerated consecutively from 1 through 20 provide for various aspects of the present invention. In one embodiment, in a first paragraph (1), the present invention provides a treated alloy composition comprising cobalt, nickel and chromium, wherein alloy surface does not contain nickel or cobalt within the first 10 nm of the depth of the surface.

2. The treated alloy composition of paragraph 1, wherein the alloy surface does not contain nickel or cobalt within the first 5 nm of the depth of the surface.

3. The treated alloy composition of paragraph 2, wherein the alloy surface is devoid of nickel or cobalt is at least 2 nm in depth.

4. The treated alloy composition of any of paragraphs 1 through 3, wherein the alloy is configured as a spring or an electrical lead.

5. The treated alloy composition of paragraph 4, wherein the spring or electrical lead is in a medical device.

6. The treated alloy composition of paragraph 5, wherein the medical device is a drug pump.

7. A treated alloy composition comprising cobalt, nickel and chromium, where the alloy releases less than 1 $ng/mm^2$ of cobalt or nickel over a 16 week period at 37° C. in an aqueous nitric acid solution at a pH of 2.2.

8. The treated alloy composition of paragraph 7, wherein the alloy surface is treated with about 15 to about 30 percent nitric acid by volume at a temperature of from about 20° C. to about 100° C. for a period of time from about 30 minutes to about 120 minutes.

9. The treated alloy composition of either of paragraphs 7 or 8, wherein the surface treatment reduces the nickel or cobalt concentration through a depth of about 10 nm from the surface of the alloy.

10. The treated alloy composition of any of paragraphs 7 through 9, wherein the surface treatment reduces the nickel or cobalt concentration through a depth of about 5 nm of the surface of the alloy.

11. The treated alloy composition of paragraph 10, wherein the alloy surface is devoid of nickel or cobalt is at least 2 nm in depth.

12. The treated alloy composition of any of paragraphs 7 through 11, wherein the alloy is configured as a spring or an electrical lead.

13. The treated alloy composition of paragraph 12, wherein the spring or electrical lead is in a medical device.

14. The treated alloy composition of paragraph 13, wherein the medical device is a drug pump.

15. A method to modify a surface of a cobalt, nickel and chromium alloy, wherein the alloy surface is treated comprising the step:
treating the alloy with about 15 to about 30 percent nitric acid by volume at a temperature of from about 20° C. to about 100° C. for a period of time from about 30 minutes to about 120 minutes.

16. The method of paragraph 15, further comprising the step of rinsing the alloy surface with water after the nitric acid treatment 17. The method of either paragraph 15 or 16, wherein the surface of the alloy releases less than 1 $ng/mm^2$ cobalt or nickel over a 16 week period at 37° C. in an aqueous nitric acid solution at a pH of 2.2.

18. The method of any of paragraphs 15 through 17, wherein the surface treatment reduces the nickel or cobalt concentration through a depth of about 10 nm of the surface of the alloy.

19. The method of any of paragraphs 15 through 17, wherein the surface treatment reduces the nickel or cobalt concentration through a depth of about 5 nm of the surface of the alloy.

20. The method of paragraph 19, wherein the surface treatment reduces the nickel or cobalt to at least 2 nm in depth.

The invention will be further described with reference to the following non-limiting Examples. It will be apparent to those skilled in the art that many changes can be made in the embodiments described without departing from the scope of the present invention. Thus the scope of the present invention should not be limited to the embodiments described in this application, but only by embodiments described by the language of the claims and the equivalents of those embodiments. Unless otherwise indicated, all percentages are by weight.

EXAMPLES

The following studies characterize and compare the effect of chemical treatment of 30 vol % nitric acid on the long-term metal ion release kinetics of MP35N low Ti Over Pressure Mechanism (OPM) springs. Data generated is applicable to valve spring and return springs in implantable infusion systems as well because MP35N low Ti material is used for such springs. The test is a static soak test, also known as an immersion test.

Table 1 lists the physical properties of the springs used in this study.

TABLE 1

| Spring Identification and Surface Area | | | |
|---|---|---|---|
| Material | Configuration | Surface Area ($mm^2$) | Supplier |
| MP35N low Ti Spring | Helical spring | 118.65 | Heraeus |

MP35N low Ti is a cobalt based alloy, 35% Ni-35% Co-20% Cr-10% Mo with Ti<=0.01%, currently used for return springs and valve springs under evaluation for Over Pressure Mechanism (OPM) spring application Table 2 provides a test matrix, listing sample IDs, chemical treatments, test solution, and samples taken and examined at 2 weeks, 4, weeks, 8 weeks and 16 weeks. The springs were not sterilized. Sterilization process shall not affect the properties of the springs because the temperature is not sufficiently high enough to induce any physical and/or chemical changes in material.

TABLE 2

| Material ID and Testing Matrix | | | | | |
|---|---|---|---|---|---|
| MP35N Spring ID | # of Sample in Each Test Tube | Dilute Nitric Acid (pH 2.2) | | | |
| | | 2 weeks | 4 weeks | 8 weeks | 16 weeks |
| 091005-001[1] No Nitric Acid Treatment) | 1 spring/ 10 mL × 3 | X | X | X | X |
| 091005-13922[2] 1X, (1 time Nitric Acid Treatment) | 1 spring/ 10 mL × 3 | X | X | X | X |
| 091005-139[3] 2X, (2 times Nitric Acid Treatment) | 1 spring/ 10 mL × 3 | X | X | X | X |
| Control solution | 10 mL × 1 | X | X | X | X |

[1]Samples were cleaned with a 2% aqueous Micro 90 cleaning solution at 43° C., then triple rinsed with deionized water.
[2]Samples were cleaned with a 2% aqueous Micro 90 cleaning solution at 82° C., followed by a 30 vol % aqueous nitric acid cleaning at 63° C., then triple rinsed with deionized water.
[3]Samples were cleaned with a 2% aqueous Micro 90 cleaning solution at 82° C., followed by a 30 vol % aqueous nitric acid cleaning at 63° C., then triple rinsed with deionized water. The sample was then treated a second time with a 30 vol % aqueous nitric acid cleaning at 63° C., then triple rinsed with deionized water.

The following is the general procedure for the treatment of Cr/Co/Ni springs. Each spring sample was aseptically transferred into a sterile 15 mL polypropylene centrifuge tube with one single spring sample per tube. Sampling was done in triplicate for each set of treatment conditions and for each time point, e.g., at 2 weeks, 4, weeks, etc.

Into each centrifuge tube was added 10 mL of dilute nitric acid at pH 2.2, with a control sample of dilute nitric acid at pH 2.2 also prepared as background references. The samples were placed in test tube racks and set on a shaker at 100 RPM in a 37° C. incubator.

At each sampling time point, samples were removed from the incubator and the solution decanted into a sterile 15 mL polypropylene centrifuge tube. These solutions were stored in a refrigerator until all samples were taken over the 16 week period. The springs were then rinsed with deionized water and dried for surface analysis.

All sample solutions were submitted to Braun Intertec Corp. Analytical Lab for metals analysis by Inductively Coupled Plasma-Mass Spectrometer; multi-elemental trace level analysis (ICP-MS).

Three samples listed below were submitted for X-ray photoelectron spectroscopy (XPS) analysis for surface chemistry and depth profiling.

Sample 1: Control: cleaned one time with a 2% aqueous Micro 90 cleaning solution at 43° C., then triple rinsed with deionized water.

Sample 2: cleaned one time with a 2% aqueous Micro 90 cleaning solution at 82° C., followed by a 30 vol % aqueous nitric acid cleaning at 63° C., then triple rinsed with deionized water.

Sample 3: The sample was cleaned with a 2% aqueous Micro 90 cleaning solution at 82° C., followed by a 30 vol % aqueous nitric acid cleaning at 63° C., then triple rinsed with deionized water. The sample was again cleaned with a 30 vol % aqueous nitric acid cleaning at 63° C., then triple rinsed with deionized water.

X-ray photoelectron spectroscopy (XPS) is also known as Electron spectroscopy for chemical analysis (ESCA). A survey spectrum to determine all elements present (except H) was first acquired from each sample. The spectra were used to obtain quantitative surface composition by integrating the areas under the photoelectron peaks and applying empirical sensitivity factors. High-resolution spectra can also be acquired for elements identified in the survey spectra. The high-resolution scans can reveal binding energy shifts, which often contain useful chemical information. The depth of analysis of this technique is on the order of about 75 Å. The physical parameters are provided below.

| | |
|---|---|
| Instrument | Physical Electronics VersaProbe XPS |
| X-ray source | Monochromatic Al Kα |
| Analysis area | 20 micron spot for profiles, 100 micron for spectra |
| Take-off angle | 45 degrees |
| Charge correction | C—C, C—H in C 1s spectra set to 284.8 eV |
| Sputter Conditions | Ar$^+$ ions, 2 kV beam, 500 nA, 3 × 3 mm raster |

The sputter rate at these conditions was approximately 2.1 nm/min on $SiO_2$. Sputter rates are material dependent. Survey and high resolution spectra were obtained from three areas on the OD of each spring and a depth profile was obtained from one area on the OD of each spring.

Metals Analysis

The solutions were analyzed at Braun Intertec Analytical Lab (a qualified 3rd party analytical lab) using a Perkin Elmer Elan DRC-E ICP-MS following EPA Method 200.8 for trace metals determination in aqueous environments.

Results were calculated by subtracting the control level, normalizing for total volume, and dividing the surface area of the spring using the equation illustrated below:

$$((\mu g/L_{Solution} - \mu g/L_{Control}) \times Volume)/Surface\ area;\ then\ converted\ to\ (ng/mm^2)$$

The results graphed are the average of the triplicate preparation for each treatment at each time point.

FIG. 1 summarizes the metal ion release data, showing the comparison among different treatments. It was evident that the $HNO_3$ treatment of the MP35N low Ti spring did decrease the release of cobalt and nickel significantly by a factor of over 20. The ICP data on 3 replicates were fairly consistent with low standard deviations (STDEV). For the three replicate samples at each time point that did not receive nitric acid treatment, the STDEVs for Co were 0.97 ng/mm$^2$ at 2 week, 0.49 ng/mm$^2$ at 4 week, 0 ng/mm$^2$ at 8 week, and 1.29 ng/mm$^2$ at 16 week and the STDEVs for Ni were 0.49 ng/mm$^2$ at 2 week, 1.29 ng/mm$^2$ at 4 week, 0.49 ng/mm$^2$ at 8 week, and 0.84 ng/mm$^2$ at 16 week, respectively.

Figure 2:
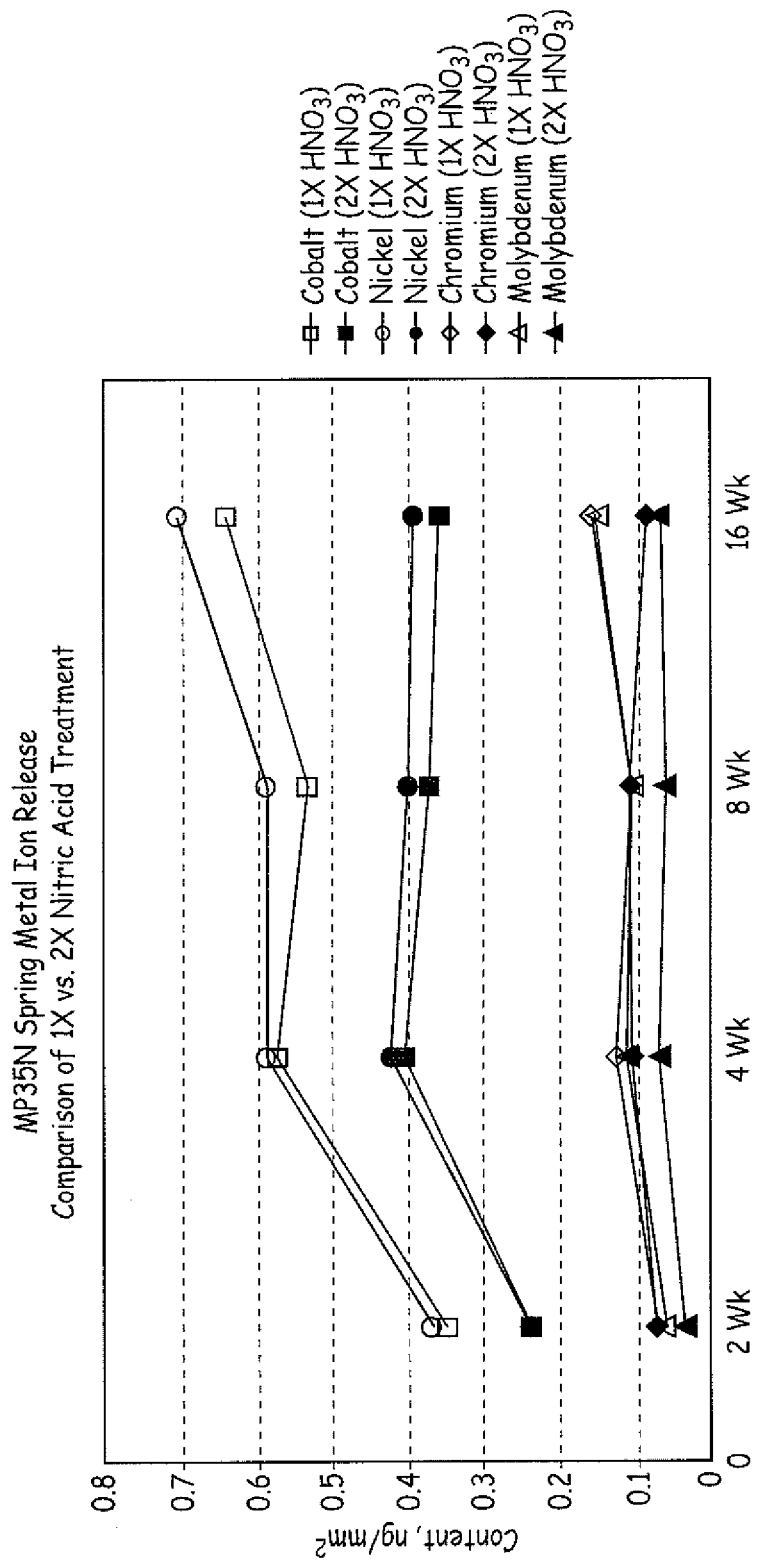
FIG. 2 provides comparison of data between the 1× nitric acid treatment and 2× nitric acid treatments.

FIG. 2 shows the comparison of the nitric acid treatment once vs. nitric acid treatment twice. It appears that application of nitric acid treatment twice further reduced the release of cobalt and nickel by approximately 30%.

XPS Surface Analysis and Depth Profiling

Table 3 provides the relative atomic percent (at %) of the elements detected on the surfaces of the samples. The first region for the 1× cleaned sample was unintentionally sputtered on before acquisition, rendering the data un-useful for this analysis. It is common in XPS analysis to observe approximately 20 at % C due to adventitious hydrocarbons adsorbing to the surface. The level of C on the samples was higher than that, suggesting some other source of organic foreign material. The 0 was present due to the oxide layer of the metal, and it was also potentially a component in the organic foreign material. Low levels of Cl were seen on the samples. Cl is a common contaminant associated with handling of samples. The constituent metals of MP35N (Cr, Co, Ni, and Mo) were observed on all the samples. The control sample had much higher concentrations of Co and Ni at the surface as compared to samples that were treated one or two times with the procedures as described above with nitric acid. (Control samples were treated one time with a 2% aqueous Micro 90 cleaning solution at 43° C., then triple rinsed with deionized water.)

TABLE 3

Relative Atomic % Determined from XPS Survey Spectra.

| | at % C | at % O | at % Cl | at % Cr | at % Co | at % Ni | at % Mo |
|---|---|---|---|---|---|---|---|
| Control | 50.9 | 34.0 | 0.8 | 0.6 | 7.2 | 6.3 | 0.3 |
| Control | 54.8 | 30.2 | 0.7 | 0.6 | 7.7 | 6.0 | 0.0 |
| Control | 45.0 | 34.7 | 0.8 | 1.2 | 10.0 | 8.2 | 0.1 |
| avg | 50.2 | 33.0 | 0.8 | 0.8 | 8.3 | 6.8 | 0.1 |
| std | 4.9 | 2.4 | 0.0 | 0.3 | 1.5 | 1.2 | 0.1 |
| Cleaned 1x | N/A | N/A | N/A | N/A | N/A | N/A | N/A |
| Cleaned 1x | 29.8 | 46.4 | 0.6 | 16.1 | 1.5 | 2.2 | 3.4 |
| Cleaned 1x | 26.6 | 47.8 | 0.5 | 17.5 | 2.2 | 1.6 | 3.9 |
| avg | 28.2 | 47.1 | 0.5 | 16.8 | 1.9 | 1.9 | 3.7 |
| std | 2.3 | 1.0 | 0.1 | 1.0 | 0.4 | 0.4 | 0.4 |
| Cleaned 2x | 38.9 | 41.9 | 0.3 | 13.4 | 1.6 | 1.0 | 2.9 |
| Cleaned 2x | 50.0 | 35.4 | 0.5 | 10.4 | 1.0 | 0.5 | 2.2 |
| Cleaned 2x | 40.1 | 42.4 | 0.1 | 13.0 | 0.9 | 0.7 | 2.9 |
| avg | 43.0 | 39.9 | 0.3 | 12.3 | 1.2 | 0.7 | 2.7 |
| std | 6.0 | 3.9 | 0.2 | 1.6 | 0.4 | 0.3 | 0.4 |

The composition of the oxide layer is reported below in Table 4, factoring out the 0 contribution and only quantifying the metal atoms. The Cr oxide state was not well defined from the data. Many Cr oxides and hydroxides overlap in binding energy. The samples had very similar looking spectra, suggesting similar species were present. The Ni oxide species was consistent with reference data for Ni(II). Many Co oxides and hydroxides overlap, so the Co oxide signal was nonspecific. Three distinct Mo species were identified, Mo(IV), Mo(IV)-hy, and Mo(VI). These three Mo species were individually quantified. The control sample's oxide layer was primarily made up of Co and Ni species. The cleaned samples had primarily Cr species in the oxide, and they were richer in Mo species. The 1× and 2× cleaned samples were fairly similar, though there may have been some subtle changes in the relative amounts of Mo species.

For example, Table 4 demonstrates that the percentage of Co/Ni at the surface is from approximately 92% (total Co/Ni) to about 10% after 1 or 2 times of nitric acid treatment as described herein.

TABLE 4

Relative at % of Metals in the Oxide Layer Determined from XPS High Resolution Spectra.

|  | at % Cr(ox/hy) | at % Co(ox/hy) | at % Ni(II) | at % Mo(IV) | at % Mo(IV-hy) | at % Mo(VI) |
|---|---|---|---|---|---|---|
| Control | 8 | 54 | 38 | 0 | 0 | 0 |
| Control | 7 | 46 | 46 | 0 | 0 | 0 |
| Control | 8 | 51 | 40 | 0 | 0 | 1 |
| avg | 7 | 51 | 41 | 0 | 0 | 0 |
| std | 0.6 | 3.9 | 4.4 | 0.0 | 0.1 | 0.1 |
| Cleaned 1x | N/A | N/A | N/A | N/A | N/A | N/A |
| Cleaned 1x | 82 | 6 | 5 | 2 | 2 | 3 |
| Cleaned 1x | 84 | 4 | 4 | 2 | 3 | 4 |
| avg | 83 | 5 | 4 | 2 | 3 | 4 |
| std | 1.7 | 1.7 | 0.8 | 0.2 | 0.2 | 0.4 |
| Cleaned 2x | 84 | 4 | 4 | 2 | 1 | 5 |
| Cleaned 2x | 88 | 1 | 3 | 1 | 1 | 5 |
| Cleaned 2x | 83 | 5 | 5 | 2 | 1 | 4 |
| avg | 85 | 3 | 4 | 2 | 1 | 5 |
| std | 2.7 | 1.8 | 1.1 | 0.3 | 0.1 | 0.6 |

Sputter depth profiles were performed on one area of each spring. The results are displayed below in FIGS. 3, 4, and 5.

Figure 3:
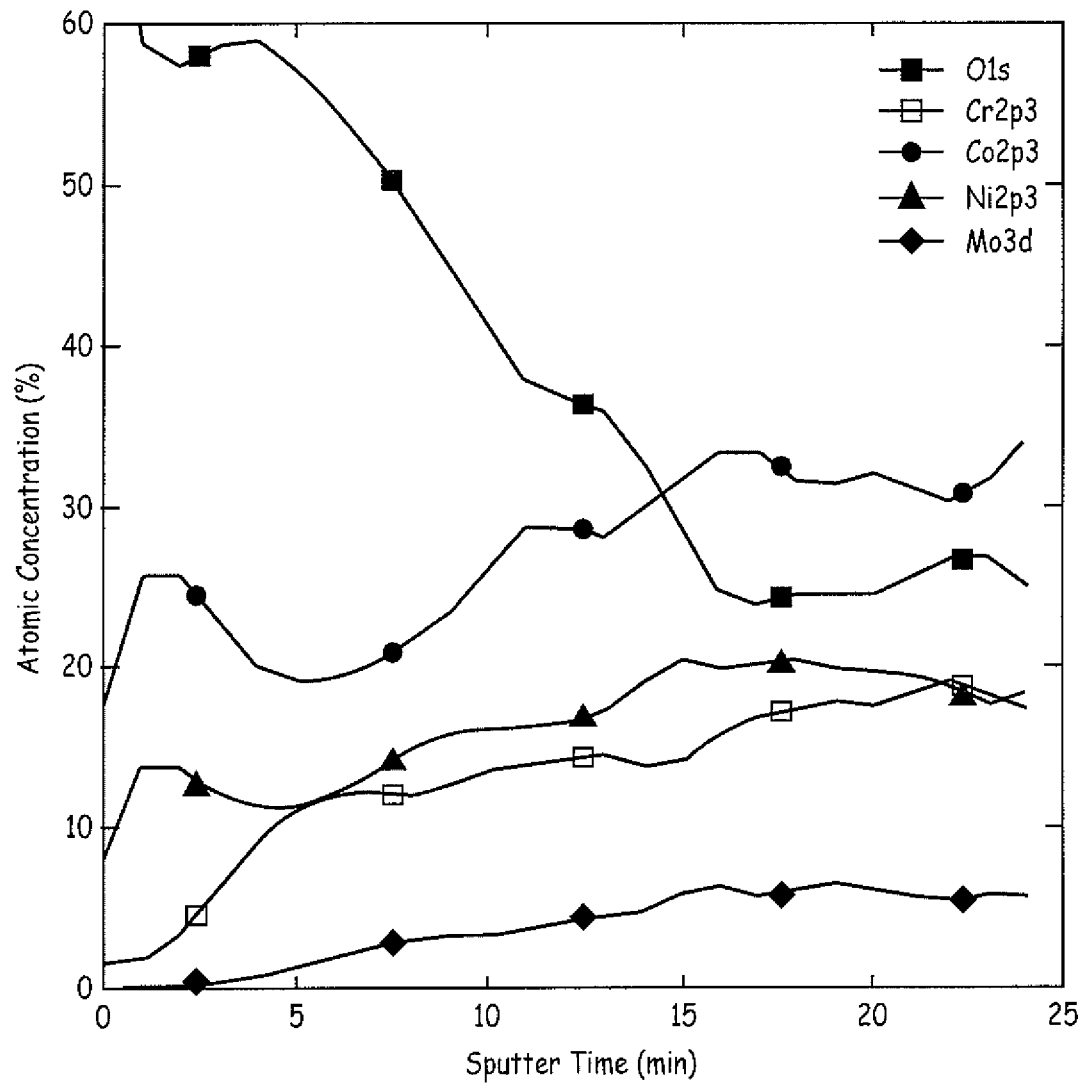
FIG. 3 provides XPS depth profiling of a MP35N low Ti sample that did not receive nitric acid chemical treatment.
Figure 4:
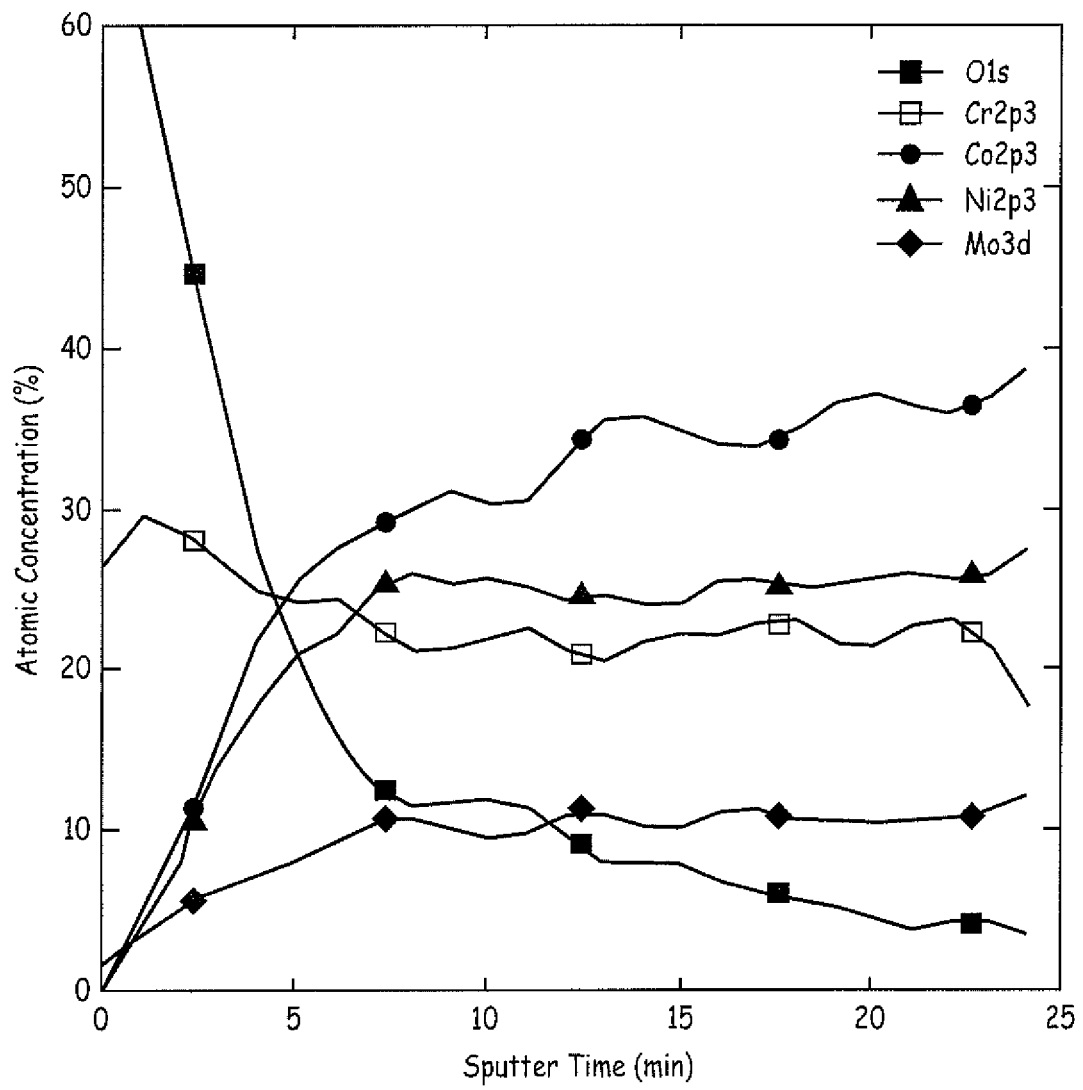
FIG. 4 provides XPS depth profiling of a MP35N low Ti sample that received 1× nitric acid chemical treatment. A Ni and Co depleted surface layer, up to 5 nm, can be observed.

FIG. 3 shows the samples after treatment with only a 2% aqueous Micro 90 cleaning solution at 43° C., then triple rinsed with deionized water. FIG. 4 represents samples after treatment cleaned one time with a 2% aqueous Micro 90 cleaning solution at 82° C., followed by a 30 vol % aqueous nitric acid cleaning at 63° C., then triple rinsed with deionized water.

Figure 5:
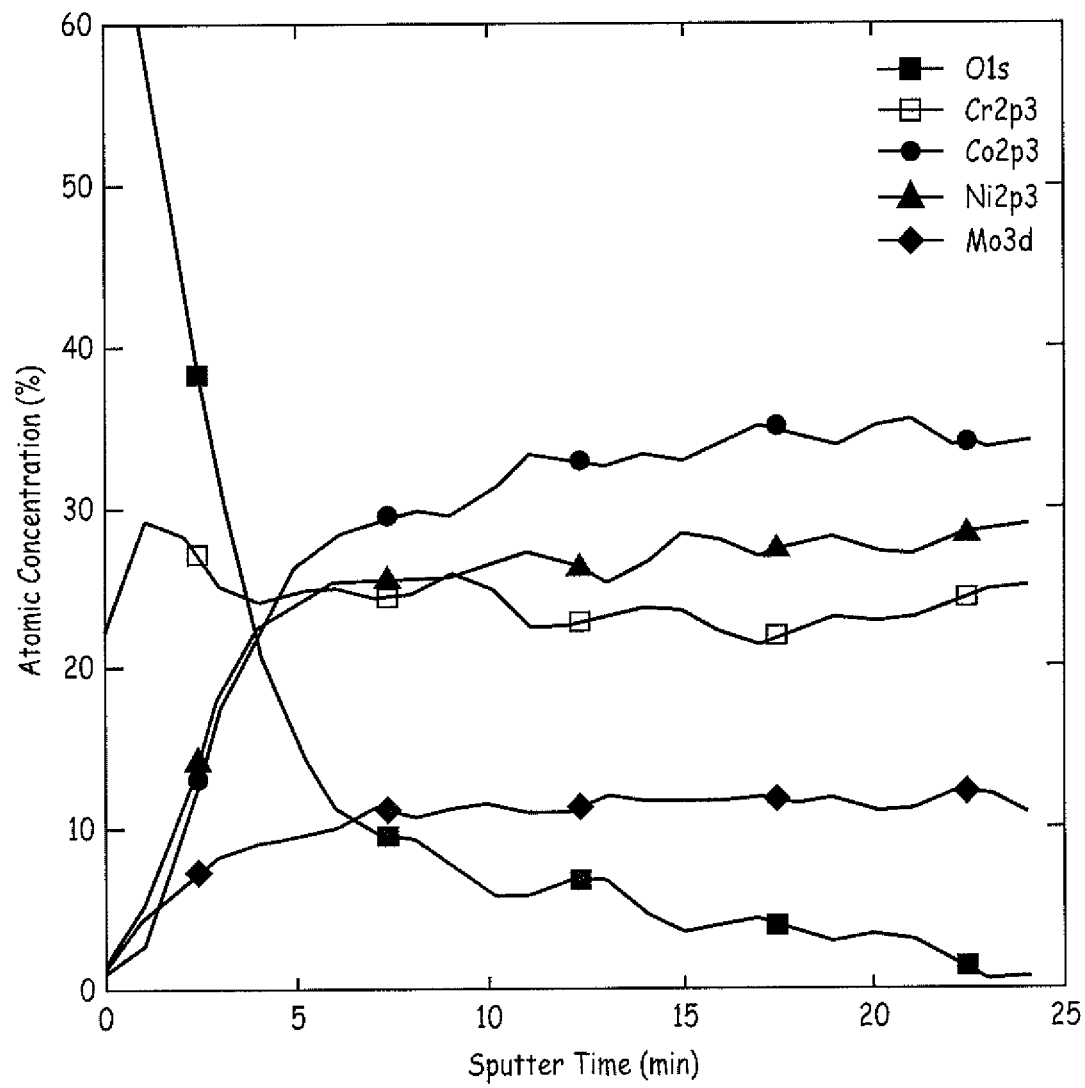
FIG. 5 provides XPS depth profiling of a MP35N low Ti sample that received 2× nitric acid chemical treatments. A Ni and Co depleted surface layer, up to 5 nm, can be observed.

FIG. 5 represents samples cleaned with a 2% aqueous Micro 90 cleaning solution at 82° C., followed by a 30 vol % aqueous nitric acid cleaning at 63° C., then triple rinsed with deionized water. The samples were again cleaned with a 30 vol % aqueous nitric acid cleaning at 63° C., then triple rinsed with deionized water.

The round surface and any surface roughness can result in broadening of the profiles. C was largely removed after the first sputter cycle and so was not reported in these figures. All the samples were very rich in 0 near the surface, consistent with the expected oxide layer. The control sample had large concentrations of Ni and Co near the surface, while the Cr and Mo increased slowly with depth. The oxide was quite thick in this sample, with the 0 never getting depleted, even after 25 min of sputtering. If the sputter rate of $SiO_2$ is applied, this represents approximately 50 nm of sputtering depth. The cleaned samples had very similar profiles to each other, but different from the control. They both were very rich in Cr near the surface. Ni and Co were significantly lower during the first 5 min of sputtering compared to their bulk concentration. Due to the suspected broadening effects mentioned above, it is appropriate to report on when the levels of Co and Ni rose to half of their stable values. This occurred around 2.5 min of sputtering. Again, if the sputter rate of $SiO_2$ is applied, this represents approximately 5 nm to 10 nm of sputtering depth (based on an $SiO_2$ rate of sputter at 2.1 nm/minute for MP35N low titanium material.).

Although the present invention has been described with reference to preferred embodiments, persons skilled in the art will recognize that changes may be made in form and detail without departing from the spirit and scope of the invention. All references cited throughout the specification, including those in the background, are incorporated herein in their entirety. Those skilled in the art will recognize, or be able to ascertain, using no more than routine experimentation, many equivalents to specific embodiments of the invention described specifically herein. Such equivalents are intended to be encompassed in the scope of the following claims.

What is claimed is:

1. A treated alloy composition comprising cobalt, nickel, molybdenum and chromium, wherein the alloy surface has increased concentrations of molybdenum and chromium within at least the first 2 nm of the depth of the surface, wherein the alloy surface concentration of molybdenum is from about 2.2 atomic percent to about 3.9 atomic percent and the concentration of chromium is from about 10.4 atomic percent to about 17.5 atomic percent.

2. The treated alloy composition of claim 1, wherein the alloy surface has increased concentrations of molybdenum and chromium within the first 5 nm of the depth of the surface.

3. The treated alloy composition of claim 2, wherein the alloy surface has increased concentrations of molybdenum and chromium at least 10 nm in depth.

4. The treated alloy composition of claim 1, wherein the alloy is configured as a spring or an electrical lead.

5. The treated alloy composition of claim 4, wherein the spring or electrical lead is in a medical device.

6. The treated alloy composition of claim 5, wherein the medical device is a drug pump.

7. The treated alloy composition of claim 1, wherein the alloy surface is pretreated with an alkaline aqueous solution containing about 0.01 percent to about 10 percent surfactants and chelating agents by weight.

8. A treated alloy composition comprising cobalt, nickel, molybdenum and chromium, wherein the alloy surface has increased concentrations of molybdenum and chromium, wherein the alloy surface concentration of molybdenum is from about 2.2 atomic percent to about 3.9 atomic percent and the concentration of chromium is from about 10.4 atomic percent to about 17.5 atomic percent, and wherein the alloy releases less than 1 $ng/mm^2$ of cobalt or nickel over a 16 week period at 37° C. in an aqueous nitric acid solution at a pH of 2.2.

9. The treated alloy composition of claim 8, wherein the alloy surface is treated with about 15 to about 30 percent nitric acid by volume at a temperature of from about 40° C. to about 100° C. for a period of time from about 60 minutes to about 180 minutes.

10. The treated alloy composition of claim 8, wherein the treated surface of has increased concentrations of molybdenum and chromium through a depth of about 2 nm from the surface of the alloy.

11. The treated alloy composition of claim 8, wherein the treated surface has increased concentrations of molybdenum and chromium through a depth of about 5 nm of the surface of the alloy.

12. The treated alloy composition of claim 11, wherein the alloy surface has increased concentrations of molybdenum and chromium at least 10 nm in depth.

13. The treated alloy composition of claim 8, wherein the alloy is configured as a spring or an electrical lead.

14. The treated alloy composition of claim 13, wherein the spring or electrical lead is in a medical device.

15. The treated alloy composition of claim 14, wherein the medical device is a drug pump.

16. A method to modify a surface of a cobalt, nickel, molybdenum and chromium alloy as claimed in claim 1, wherein the alloy surface is treated to have increased concentrations of molybdenum and chromium, wherein the alloy surface concentration of molybdenum is from about 2.2 atomic percent to about 3.9 atomic percent and the concentration of chromium is from about 10.4 atomic percent to about 17.5 atomic percent, comprising the step:

treating the alloy with about 15 to about 30 percent nitric acid by volume at a temperature of from about 40° C. to about 100° C. for a period of time from about 60 minutes to about 180 minutes.

17. The method of claim 16, further comprising the step of rinsing the alloy surface with water after the nitric acid treatment.

18. The method of claim 16, wherein the surface of the alloy releases less than 1 $ng/mm^2$ cobalt or nickel over a 16 week period at 37 ° C. in an aqueous nitric acid solution at a pH of 2.2.

19. The method of claim 16, wherein the surface has increased concentrations of molybdenum and chromium through a depth of about 10 nm of the surface of the alloy.

20. The method of claim 16, wherein the surface has increased concentrations of molybdenum and chromium through a depth of about 5nm of the surface of the alloy.

21. The method of claim 20, wherein the surface has increased concentrations of molybdenum and chromium to at least 2 nm in depth.

22. The method of claim 16, further comprising the step:
pretreating the alloy surface with an alkaline aqueous solution containing about 0.01 percent to about 10 percent surfactants and chelating agents by weight at a temperature of from about 37° C. to about 71° C. for a period of time from about 30 minutes to about 120 minutes.

* * * * *